(12) United States Patent
Topfer et al.

(10) Patent No.: US 7,480,365 B1
(45) Date of Patent: Jan. 20, 2009

(54) DOSE REDUCED DIGITAL MEDICAL IMAGE SIMULATIONS

(75) Inventors: Karin Topfer, Rochester, NY (US); Jacquelyn S. Ellinwood, Rochester, NY (US)

(73) Assignee: Carestream Health, Inc., Rochester, NY (US)

( * ) Notice: Subject to any disclaimer, the term of this patent is extended or adjusted under 35 U.S.C. 154(b) by 0 days.

(21) Appl. No.: 11/834,286

(22) Filed: Aug. 6, 2007

(51) Int. Cl.
H05G 1/44 (2006.01)
(52) U.S. Cl. .................. 378/108; 378/97; 378/98.12
(58) Field of Classification Search .................. 378/96, 378/97, 98.12, 108
See application file for complete search history.

(56) References Cited

U.S. PATENT DOCUMENTS

| 5,396,531 | A | 3/1995 | Hartley | |
|---|---|---|---|---|
| 2002/0085673 | A1* | 7/2002 | Rinaldi et al. | 378/108 |

OTHER PUBLICATIONS

P. Massoumzadeh et al., Noise Simulation in X-Ray CT, Proceedings of SPIE, vol. 5745, Medical Imaging 2005; Physics of Medical Imaging, pp. 898-909.
P. Timberg et al., Potential for Lower Absorbed Dose in Digital Mammography: A JAFROC Experiment Using Clinical Hybrid Images with Simulated Dose Reduction, Proceedings of SPIE, vol. 6146, Medical Imaging 2006; Image Perception, Observer Performance, and Technology Assessment, 614614, Mar. 17, 2006.
A.V. Oppenheim and R. W. Schafer, Discrete-Time Signal Processing, Englewood Cliffs, NJ, Prentice-Hall, 1989, pp. 311-312.
IEC-62220-1 Standard, Medical Electrical Equipment—Characteristics of Digital X-Ray Imaging Devices—Part 1: Determination of the Detective Quantum Efficiency, International Electrotechnical Commission (IEC), Geneva, Switzerland, 2003.
B. W. Keelan et al., Relative Impact of Detector Noise and Anatomical Structure on Lung Nodule Detection, Proc. SPIE, vol. 5372, pp. 230-241, 2004.
J.C. Dainty and R. Shaw, Image Noise Analysis and the Wiener Spectrum, Image Science, Academic Press, New York, 1974, Chapter 8.
M.P. Eckstein et al., A Practical Guide to Model Observers for Visual Detection in Synthetic and Natural Noise Images, Handbook of Medical Imaging: vol. 1, Physics and Psychophysics, Chapter 10, p. 593, SPIE Press, Bellingham, 2001.
K. Topfer et al., Advanced System Model for the Prediction of the Clinical Task Performance of Radiographic Systems, Proc. SPIE, vol. 6515, 651512, 2007.

* cited by examiner

Primary Examiner—Chih-Cheng G Kao

(57) ABSTRACT

A method for providing a reduced exposure value for radiographic imaging obtains a set of flat-field images at two or more exposure values and measures the noise power spectra using the flat field images. At least one noise table is generated according to interpolated noise power spectra for a set of predetermined exposure values. Values from the at least one noise table are applied to a clinical image to form a reduced exposure simulation image. A noise mask is generated according to at least one noise table and the exposure values of the reduced exposure simulation image and added to the reduced exposure simulation image. The reduced exposure simulation image is assessed to generate a desired dose reduction factor.

19 Claims, 7 Drawing Sheets

STANDARD IEC 62220-1 SPECTRA

| SPECTRUM | kVp | ADDED FILTRATION (mm Al) | HVL (mm Al) |
|---|---|---|---|
| RQA 3 | 50 | 10 | 4.0 |
| RQA 5 | 70 | 21 | 7.1 |
| RQA 7 | 90 | 30 | 9.1 |
| RQA 9 | 120 | 40 | 11.5 |

*FIG. 5*

DOSE REDUCED DIGITAL MEDICAL IMAGE SIMULATIONS

FIELD OF THE INVENTION

This invention generally relates to diagnostic imaging and more particularly relates to a method for simulating a reduced dose digital medical image that can be used for determining a low achievable radiation level for a given diagnostic task.

BACKGROUND OF THE INVENTION

While x-rays have significant value for diagnosing the condition of a patient, ionizing X-ray radiation can be harmful to living tissue. Accordingly, with the intent of reducing radiation risks wherever possible, the International Commission on Radiological Protection (ICRP), beginning in 1977, has proposed that a policy of ALARA (As Low As Reasonably Achievable) be adopted for radiological personnel and, more recently, for patients who undergo x-ray imaging.

To address this problem, manufacturers and users of x-ray equipment have expended efforts in developing both threshold settings and procedural techniques that help to reduce exposure levels. For example, technique charts that provide recommended exposure settings for various conditions can be developed to meet the ALARA objective. These reduced settings may then be used for system tools that help to control dose levels, such as automatic exposure control (AEC), and anatomical programmed radiography (APR).

While exposure reduction is a worthwhile goal, however, its implementation should not compromise the capabilities that radiological imaging systems offer to the diagnostician. Incorrectly reducing X-ray exposure levels may result in poor quality images with reduced diagnostic value. Images produced with too little exposure can be characterized by problems such as excessive graininess and low contrast. Such images may be difficult to use and could potentially compromise diagnosis. In some cases, problems such as these require images to be re-taken.

One solution for defining the exposure level that minimizes patient exposure without compromising diagnostic image quality is reduced-dose image simulation. Advantages of simulation over other approaches are 1) generation of an image without additional exposure to the patient, 2) exploration of a range of exposure levels without risk of compromised diagnosis, and 3) evaluation of numerous patient types and pathologies.

One proposed solution for reduced-dose image simulation in fluoroscopy, described in U.S. Pat. No. 5,396,531 entitled "Method of Achieving Reduced Dose X-Ray Fluoroscopy by Employing Statistical Estimation of Poisson Noise" by Hartley, relates to an interactive method for dose adjustment. This method calculates a dose level for each successive fluoroscopic image in a series based on a given signal-to-noise (S/N) ratio. In the method, image noise power spectrum (NPS) is assumed to be proportional to intensity (exposure) and to be spatial-frequency independent. However, this simplified noise model does not appear to adequately characterize noise, which is considered to have a more complex relationship to exposure and to spatial frequency in many cases, as described subsequently in the detailed description of the invention.

A proposed solution for reduced-dose image simulation in Computed Tomography (CT) imaging has been described in the article entitled "Noise simulation in x-ray CT" by Parinaz Massoumzadeh, Orville A. Earl, and Bruce R. Whiting, in Proceedings of SPIE, Volume 5745, Medical Imaging 2005: Physics of Medical Imaging, pp. 898-909. As with the method of Hartley, this method asserts that noise is spatial frequency independent and does not characterize image noise in more general cases.

Other proposed solutions use image simulation techniques to identify suitable levels for reduced exposure under given conditions. One example method is described in the paper entitled "Potential for lower absorbed dose in digital mammography: A JAFROC experiment using clinical hybrid images with simulated dose reduction" by Pontus Timberg, Mark Ruschin, Magnus Bath, Bengt Hemdal, Ingvar Andersson, Soren Mattsson, Dev Chakraborty, Rob Saunders, Ehsan Samei, and Anders Tingberg, in Proceedings of SPIE, Volume 6146, Medical Imaging 2006: Image Perception, Observer Performance, and Technology Assessment, 614614 (Mar. 17, 2006). In this method, low dose images are simulated from high-dose images by scaling the high dose image and adding an amount of expected noise. As with Hartley, the technique proposed in the Timberg article applies a limited characterization of imaging noise to the problem. In the method proposed, noise is calculated using a simple linear scaling of NPS based on two captured flat-field reference images.

The rather simplistic characterizations of noise presented in the previously listed references may be suitable for some individual cases, for example for objects with limited exposure latitude. However, for imaging related to living tissue, noise has proven to be more complex and a more comprehensive solution is needed. For example, the linear scaling noise model assumes that the imaging system is quantum-limited, that is, dominated by the noise of the incoming X-rays, shown to have a Poisson distribution. This assumption is made in the Hartley, Massoumzadeh, and Timberg methods. However, it has been found that the noise power spectrum (NPS) for radiation images is more complex and that image noise has multiple components, including a number of components that exhibit non-linear response to dose. The response that is proportionate to dosage is only one factor for consideration.

While a simple model may be suitable in comparing image noise against a threshold value, however, it is not suited for producing accurate low-dose image simulations from a higher-dose set of images. As a result, the type of solution proposed in Hartley, Massoumzadeh, or Timberg can be unsuitable in cases where a test image has been captured at low dosage levels, images have a large exposure latitude as, for example, in chest radiography, or where electronic noise of the detector is otherwise a significant factor.

Thus, it can be appreciated that there is a need for a simulation method that obtains its results by more accurately profiling system noise and accordingly adapts for noise impact on images captured at various dosage levels.

SUMMARY OF THE INVENTION

It is an object of the present invention to provide a method for determining reduced dose levels that meet ALARA guidelines without compromising image diagnostic quality. With this object in mind, the present invention provides a method for providing a reduced exposure value for radiographic imaging comprising: a) obtaining a set of flat-field images at two or more exposure values; b) measuring the noise power spectra using the flat field images; c) generating at least one noise table according to noise power spectra interpolated for a set of predetermined exposure values; d) transforming the exposure values of a clinical image to form a reduced exposure simulation image; e) generating a noise mask according to the at least one noise table and the exposure values of the reduced exposure simulation image; f) adding the noise mask to the reduced exposure simulation image; g) assessing the reduced exposure simulation image; and h) generating a preferred dose reduction factor.

In at least one embodiment, the present invention uses a characterization of image noise that accounts for noise components that respond differently to exposure.

An advantage of the present invention that it provides a method for reducing x-ray exposure levels using simulation data.

These and other objects, features, and advantages of the present invention will become apparent to those skilled in the art upon a reading of the following detailed description when taken in conjunction with the drawings wherein there is shown and described an illustrative embodiment of the invention.

BRIEF DESCRIPTION OF THE DRAWINGS

The foregoing and other objects, features, and advantages of the invention will be apparent from the following more particular description of the embodiments of the invention, as illustrated in the accompanying drawings. The elements of the drawings are not necessarily to scale relative to each other.

FIG. 5 is a table showing standard x-ray spectra for general radiography used in detector image quality evaluations.

DETAILED DESCRIPTION OF THE INVENTION

Figure 1:
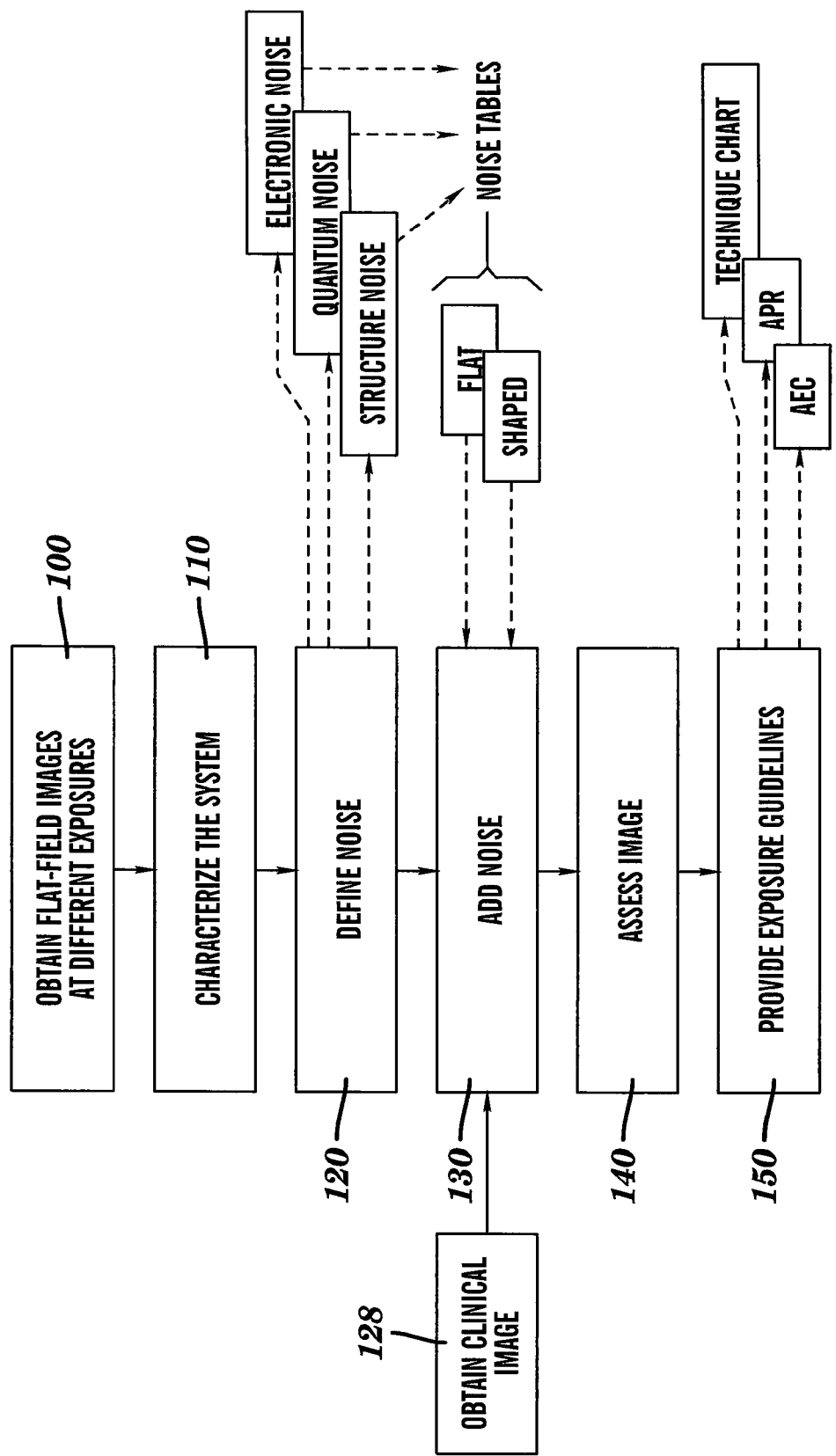
FIG. 1 is a logic flow diagram showing a method of the present invention.

The following is a detailed description of the preferred embodiments of the invention, reference being made to the drawings in which the same reference numerals identify the same elements of structure in each of the several figures.

The present description is directed in particular to elements forming part of, or cooperating more directly with, apparatus in accordance with the invention. It is to be understood that elements not specifically shown or described may take various forms well known to those skilled in the art.

The present invention provides a method for identifying reduced dose levels for radiographic and related imaging, using noise simulation. For simulating noise effects at lower dose, the method of the present invention can generate a dose that is below the dose of the captured image and is not constrained to the quantum-limited range of the X-ray detector. Thus, once the noise of the radiology imaging system has been characterized over a large exposure range, a lower dose can be simulated with high accuracy and without additional work/steps. This allows users and developers of radiology systems to generate effective technique charts and provide accurate Automatic Exposure Control (AEC) thresholds and Anatomically Programmed Radiography (APR) settings than those that have been available with earlier methods.

Referring to FIG. 1, there is shown a sequence of steps for using the method of the present invention. The steps include an obtain flat field images step 100, a system characterization step 110, a noise definition step 120, a noise adding step 130, an image assessment step 140, and a exposure guidelines step 150.

As show in FIG. 1, obtain flat field images step 100 begins the sequence. Uniform, flat field images are obtained at each of a number of settings of x-ray imaging variables such as beam energy, expressed in kiloVolt potential (kVp), filtration, e.g., using aluminum filters of various thickness, Source-Image Distance (SID) and exposure values (tube current times exposure time expressed in mAs).

Image quality characteristics of the flat-field images are obtained in a system characterization step 110.

A noise definition step 120 follows, in which NPS values are generated on a fine grid of predefined spatial frequency and exposure values based on the available measured data, so that noise tables and Finite Impulse Response (FIR) filters for image processing can be generated (Oppenheim, A. V. and R. W. Schafer, *Discrete-Time Signal Processing*, Englewood Cliffs, N.J.: Prentice-Hall, 1989, pp. 311-312). The full NPS surface can be generated using common interpolation methods, such as by bilinear or bicubic interpolation or, alternately, by fitting an analytical function to the measured data, for example.

A clinical image is obtained in an obtain clinical image step 128. The characterization information can be used to develop one or more noise tables and Finite Impulse Response (FIR) filters that can be used to add noise in a noise adding step 130.

An image assessment step 140 follows, during which results of added noise are assessed visually by a human observer and, optionally, numerically using a computational observer model.

A provide exposure guidelines step 150 is performed, providing results that can be used to develop technique charts, AEC settings, or APR settings.

Noise Characterization

The improved method of the present invention provides a more accurate characterization of noise content than has previously been used. In order to provide a better understanding of the present invention, it is initially useful to generally describe the comprehensive noise characterization that is employed.

Image noise from a system can be generally characterized by passing flat field images through the system and by measuring the Noise Power Spectrum (NPS) or the standard deviation of the output image on the detector. For the present invention, one goal is to characterize and simulate detector noise. For this purpose it is desirable to obtain this data by capturing and analyzing a number of flat-field images at different exposures, spanning the range of the digital (computed radiography (CR) or direct radiography (DR)) detector. Once these images have been captured, standard computational methods can be used to calculate a corresponding NPS according to IEC-62220-1 Standard, "Medical electrical equipment—characteristics of digital x-ray imaging devices—Part 1: determination of the detective quantum efficiency," International Electrotechnical Commission (IEC), Geneva, Switzerland, 2003.

The noise is preferably characterized under x-ray beam conditions that are typical for the exam. Depending on the exam type, different x-ray generator parameters are used. Chest x-ray exams, for example, are conducted at 110-120 kVp. Hand exams are conducted at about 60 kVp. Standard conditions under which X-ray images of different parts of the body are preferably captured are reflected in technique charts, well known to operators of this equipment.

When the radiation passes through the body, its energy spectrum changes. This is called beam hardening. Commonly additional filters are used in flat field captures to approximate the energy spectrum of the image captures. This is employed because the noise varies as a function of the beam spectrum.

As shown in the table of FIG. 5, different standard x-ray spectra have been defined in IEC-62220-1 to approximate various exam types. These x-ray spectra are related to various beam conditions. The kVp settings for RQA 3, 5, 7, and 9 correspond to approximately 50, 70, 90 and 120 respectively for a tungsten source. For example, the RQA 9 beam is generally the best approximation for chest imaging. The added Al filtration is given in the middle column of this table. The actual generator settings are varied around the nominal settings until the half value layer (HVL) given in the standard is matched. For the RQA-3 beam this means, for example, that the beam has the aim spectrum when adding 4 mm of Al reduces the intensity a factor of 2.

Noise can be characterized under one or several beam conditions as needed, according to the intended application of the equipment. Under a given beam condition, the NPS varies as a function of exposure (that is, of received dose) and as a function of spatial frequency. Discrete points of this 2-dimensional (2D) surface have been sampled in experiment. For the image simulation, it is desirable to obtain interpolated NPS values at arbitrary exposures within the exposure latitude of the detector and at spatial frequencies below the Nyquist frequency (one half of the sampling frequency). This can be achieved by common interpolation methods, for example by bilinear or bicubic interpolation, or preferably, for added robustness, by fitting an analytical function to the measured data.

As a basis for the analytical description of the 2D NPS surface, the noise was broken down into three components, which vary differently as a function of exposure:

Structure Noise: fixed pattern noise with variance proportional to exposure squared Quantum Noise: shot or Poisson noise with variance proportional to the exposure.

Electronic Noise: exposure-independent or "dark" noise.

Thus, combining these components leads to suitable equation for approximating the NPS:

$$NPS(v,E) = (SF\_SN\_1 \cdot T\_SN\_1(v)^2 + SF\_SN\_2 \cdot T\_SN\_2(v)^2) \cdot E^2 + (SF\_QN\_1 \cdot T\_QN\_1(v)^2 + SF\_QN\_2 \cdot T\_QN\_2(v)^2) \cdot E + SF\_EN\_1 \cdot T\_EN\_1(v)^2 + SF\_EN\_2 \cdot T\_EN\_2(v)^2 \quad (Eqn\ 1)$$

wherein:

E=exposure in mR;

v=spatial frequency;

SF=scale factor;

T(v)=Modulation Transfer Function or MTF;

SN/QN/EN=structure/quantum/electronic noise; and subscripts _1 and _2 indicate which of two possible contributors of each type is referenced.

In the general case, each noise contributor is allowed to have to additive terms of different magnitude and different shape (MTF). The scale factors SF and the MTF values T are obtained from the measured NPS using non-linear regression procedures. All MTF terms in Equation 1 can be parameterized for fitting using common functions, for example, Gaussian, Lorentzian, or sine functions.

The conversion of the two-dimensional NPS surface into noise tables and convolution filters that can be used in image simulations, is accomplished for example as disclosed in B. W. Keelan, K. Töpfer, J. Yorkston, W. J. Sehnert, and J. S. Ellinwood, "Relative impact of detector noise and anatomical structure on lung nodule detection," Proc. SPIE, 5372, 230-241 (2004). In this article, this conversion is summarized in the relationship given for measured NPS at an exposure E and at a spatial frequency of v cycles/mm, N(v, E).

Figure 2:
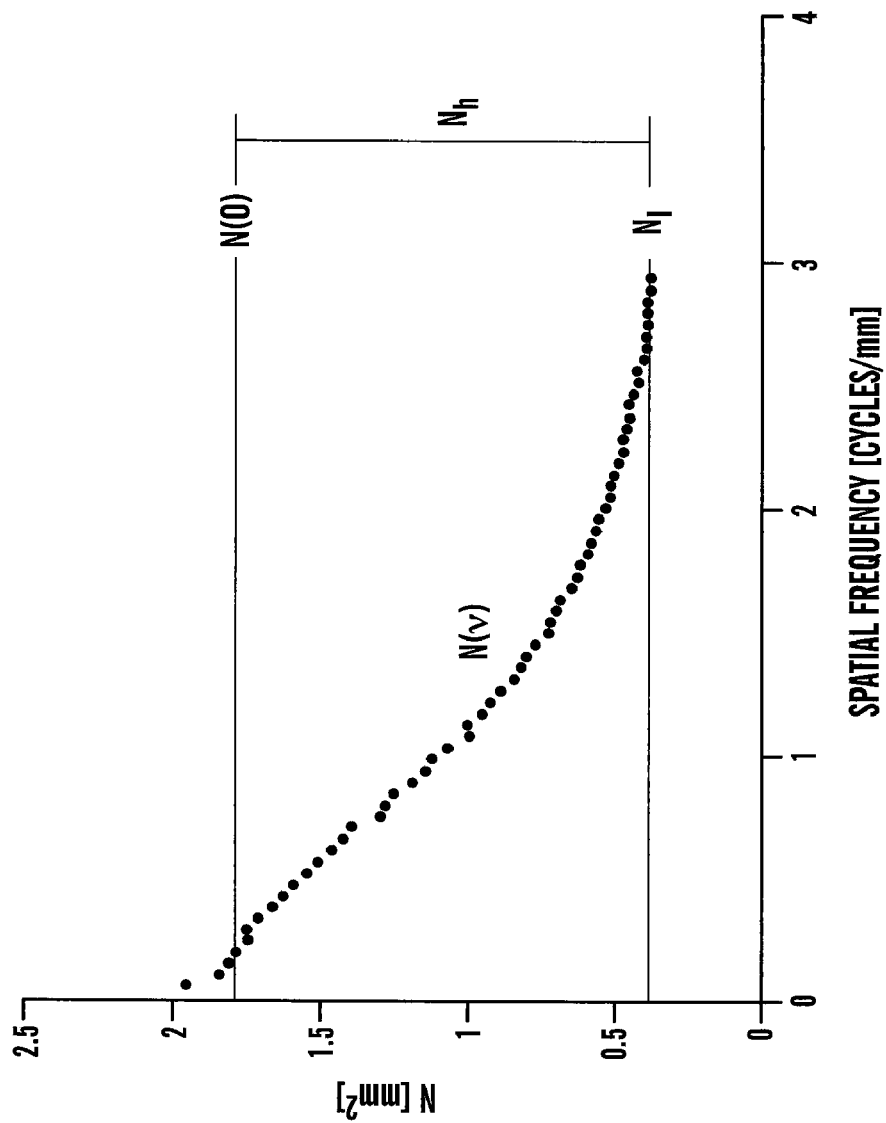
FIG. 2 is a graph showing one relationship of the noise power spectra (NPS) to spatial frequency.

FIG. 2 is a graph showing one relationship of the noise power spectra (NPS) to spatial frequency. Referring to FIG. 2, two uncorrelated contributors for noise are identified:

(1) an exposure-dependent, but frequency-independent low noise component $N_l(E)$; and (2) a high-noise, low-pass component $N_h(v, E)$.

This second component is itself separable into an exposure-dependent magnitude $N_h(E)$ and an exposure-independent shape function that is associated (using convolution) with the square of an effective Modulation Transfer Function (MTF), $M_h(v)$. This relationship can be summarized by:

$$N(v,E) = N_l(E) + [N_h(E) \cdot M_h(v)^2] \quad (Eqn.\ 2)$$

Thus, two noise tables can be provided, one corresponding to each addend in equation (2). In some cases, such as with an amorphous selenium detector, a single noise table may be sufficient.

The NPS at zero spatial frequency ($N_h+N_l$), and the NPS at Nyquist frequency, $N_l$, were obtained at each available integer detector code value (below saturation) using the fully interpolated NPS calculated according analytical expression Eqn. 1 with all relevant fit parameters. Finally, the effective low-pass MTF, $M_h(R)$, was obtained by solving Eqn. 2.

The quantities $N_l$ and $N_h$ were converted to equivalent standard deviations in ADC units, or units proportional to exposure, σ, for use in simulation noise tables, via Eqn. 3:

$$N = \sigma^2 \cdot A \quad (Eqn.\ 3)$$

where A is the pixel area (J. C. Dainty and R. Shaw, *Image Science*, Academic Press, New York, 1974, Chapter 8). The noise tables specify the standard deviations of the high and low white noise component at each detector code value (or each code value in a linearized exposure space).

In the image simulation, two noise masks are generated using a random noise generator, assuming white (frequency independent) Gaussian noise. The standard deviation at each pixel is determined by the code value in the image. The noise mask of the higher noise component is blurred by convolution with a FIR filter with response $M_h(v)$. In the most general sense, the FIR filter can be considered a frequency attenuation component. Those skilled in the art will recognize that the same blur can be achieved by applying a Fourier transform of the noise image, multiplying the result with the desired MTF, and then applying the inverse Fourier transform.

The procedure for noise simulations described by Keelan et al. was developed for images that contained no visible noise. These images were created by averaging multiple high-dose captures of suitable anthropomorphic phantoms. For the present invention, step 120 (define noise, FIG. 1) needs to be modified to take into account that the original higher dose image already contains noise.

Given these preparatory steps, the process for generating low-dose images from higher dose images can now be described, with reference to FIG. 3.

An X-ray source 20 provided with an Al filter 22 generates a series of exposures 26 to provide a flat field image 30 at each of the exposures. The NPS 40 for a given spatial frequency and exposure is calculated using this data.

Figure 3:
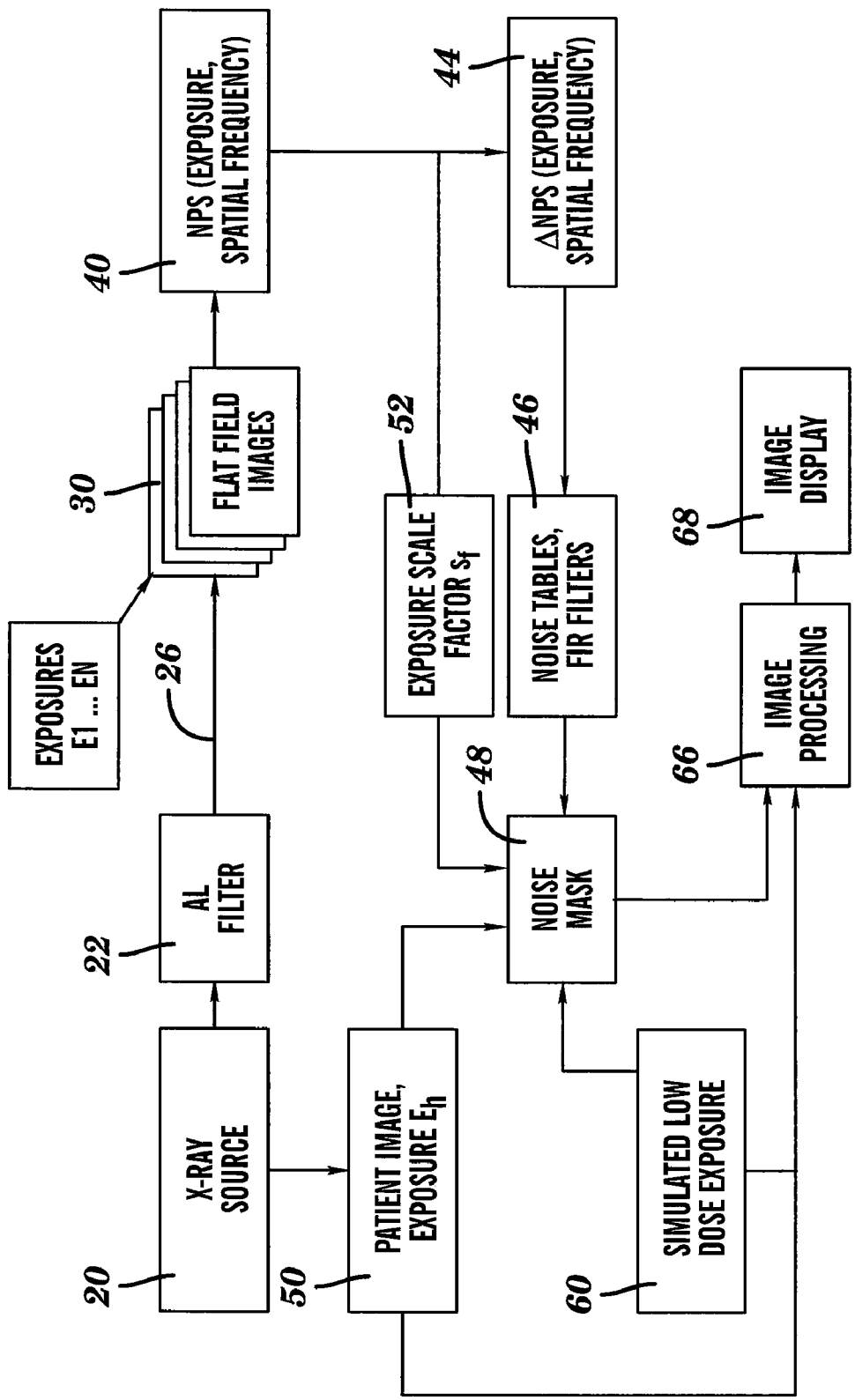
FIG. 3 is a logic flow diagram showing a process for generating low-dose images from higher dose images.

Subsequent steps in FIG. 3 then provide the simulation image. A patient image 50 at high exposure $E_h$ is obtained. Using an exposure scale factor $s_f$ 52 and the NPS 40 value, a difference NPS, ΔNPS 44 is calculated, as described below in more detail. This calculation enables noise tables and FIR filters 46 to be generated and used with exposure scale factor $s_f$ 52 to generate one or more noise masks 48, then applied to patient image 50 to obtain a simulated low-dose exposure $E_h \cdot s_f$ 60, which matches the noise magnitude and texture of a clinical exposure captured at the same lower exposure level. Image processing 66 is then applied to simulated low-dose exposure $E_h \cdot s_f$ 60 to provide an image display 68.

As for simulations when starting from noise-free images, the noise of the system is fully characterized by capturing flat field images 30 at different exposures and fitting the NPS using Eqn. 1. The high-exposure image has some residual noise, which depends on the exposure that each pixel received. The mapping from exposure to detector code value is known from the flat field characterization, and this residual noise level can be predicted from the NPS fitted value according to Eqn. 1.

If the original exposure, E, is scaled by scale factor $s_f$ 52, the residual noise in the image is also scaled down by this factor (and the NPS is scaled by the square of $s_f$). Therefore, the noise that has to be added to simulate the image noise at exposure $E \cdot s_f$ is the difference between the NPS calculated for this exposure level according to Eqn. 1 and the NPS calculated at the original exposure E multiplied by the square of $s_f$, as shown in Eqn. 4:

$$\Delta N(E \cdot s_f, R) = N(E \cdot s_f, R) - s_f^2 \cdot N(E, R) \quad \text{(Eqn. 4)}$$

This assumes that the noise sources in both images are uncorrelated. Just like an NPS fitted according to Eqn. 1, this difference in NPS is split into a frequency-dependent and a frequency independent component, which both vary as a function of exposure (Eqn. 2). Assuming the image median in log exposure is mapped to a given density in the display/print, all further image processing for the high- and low-dose captures is identical.

In the simplest case, where the code values of the clinical high exposure image 50 are proportional to exposure and no x-ray imaging parameters other than exposure are changed, the new code values of the low exposure simulation 60 can be obtained by multiplying the image 50 with the scale factor $s_f$ 52. In more general cases, it may be desired to transform the code values of the clinical image 50 to a second set of code values that is proportional to exposure using mathematical functions, or using a one-dimensional lookup table (1D LUT). The first operation can be combined with the subsequent multiplication with $s_f$ 52 into a single 1D LUT.

In more general cases, it may be desirable to simulate the low dose exposures under different x-ray imaging conditions compared with the clinical images, for example, different SID and other geometrical parameters such as x-ray tube to detector angle. In these cases the exposure scale factor 52 may depend on the position in the imaging plane. If no nonuniformities were present in the imaging plane, the exposure would reduce in proportion to the square of SID and could be accommodated with a 1D LUT or simple multiplication as discussed above. However, even if the x-ray beam is aligned with the center of the detector, the exposure on the anode side of the field of view is slightly reduced. This phenomenon is known as the Heel effect, and becomes more pronounced with decreasing SID. In this case, the exposure scale factor 52 varies as a function of the horizontal and vertical position in the imaging plane. The exposure scale factor for each original exposure E and horizontal and vertical positions x and y can be calculated using mathematical functions or using a 3-dimensional lookup table (3D LUT). In the latter case, grids are specified along the exposure and x and y axes, the exposure scale factor is calculated at all positions of the 3D grid, and the resulting 3D LUT is applied to the clinical image 50 to produce the reduced dose image, which serves as the basis for calculating the noise mask 48.

Another case of modifications in x-ray imaging parameters involves using beam energies and filtrations, for which no flat field images were obtained. Noise tables and FIR filters can be generated and stored for several relevant beam conditions. The technique chart/list of exam types will, however, contain more beam conditions than the system was characterized for. The noise simulations for those conditions are calculated from linear combinations of adjacent characterized beams. Thus, noise table values and FIR weights can be assigned to each technique chart/list of exam types entry. In newer units with automatic exposure control (AEC) it may be possible to obtain the correct weights from the generator kVp settings and the AEC data using this method.

The low-dose simulation method can be implemented in software that allows imaging physicists, technicians, technicians and/or radiologists to view clinical images at lower dose than the dose at which they were captured. The system may then store the theoretically lowest acceptable dose, then learn over time what can be used as the lowest possible dose for a given exam type and pathology in practice. AEC settings, technique chart entries, or APR guidelines can then be set or adjusted automatically using these results.

Figure 6:
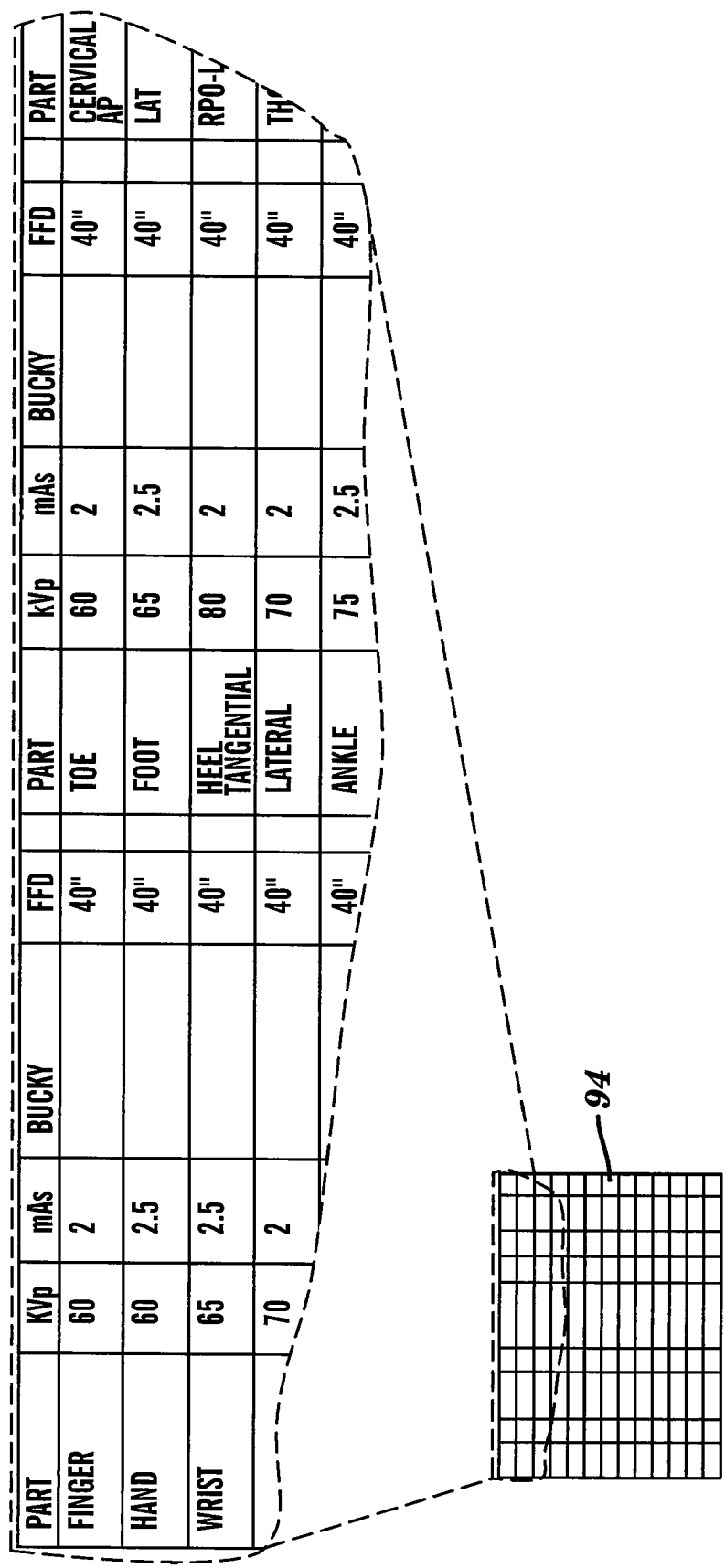
FIG. 6 is a plan view showing an example of a portion of a technique chart.

The plan view of FIG. 6 shows an enlarged portion of a technique chart 94 with some types of exposure parameters that can be generated or modified using results from the method of the present invention.

Visual Assessment of Images

Figure 7:
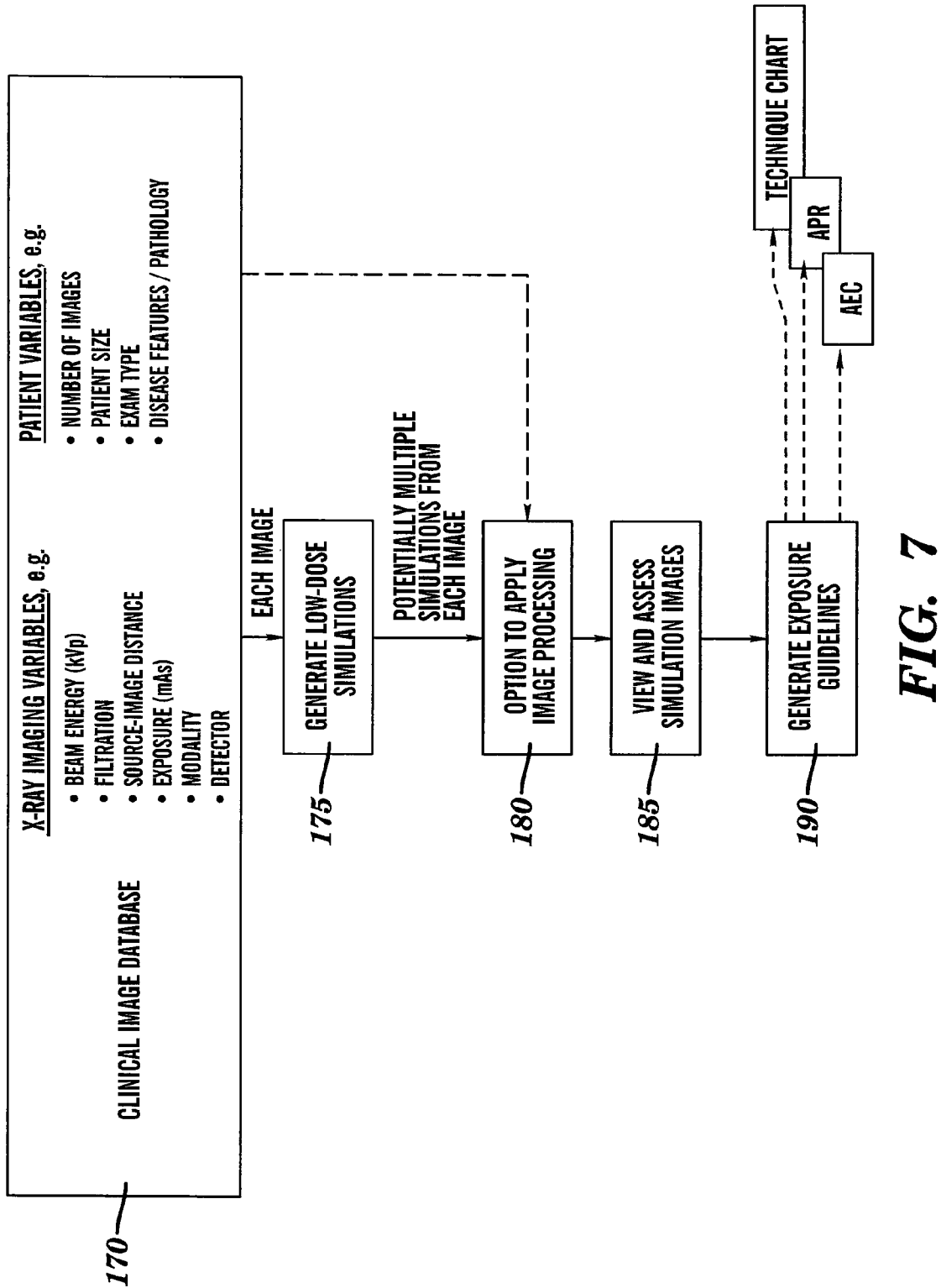
FIG. 7 is a logic flow diagram showing a process for visual assessment of low-dose simulations.

One method of determining a preferred low-dose setting uses visual assessment of low-dose simulations from clinically acquired images. The logic flow diagram illustrating a process for visual assessment of low-dose simulations is shown in FIG. 7.

The process starts from a collection of clinical images 170. Collection of images 170 represents the various types of images to which the resultant exposure settings are to be applied. Metadata on x-ray imaging variables and patient variables are stored for each image. The images may have associated X-ray imaging variables such as beam energy (kVp), filtration, source-image distance, exposure (mAs), modality (computed radiography), and detector (a-Si). Patient variables include, for example, number of images, patient size, exam type, and disease features or pathology.

Each of the clinical images of interest from the clinical image database is processed through a low-dose simulation process 175 to generate one or more low-dose image simulations. Once completed, the images to be viewed are optionally processed by image processing to enhance the presentation of the image 180 and subsequently assessed by personnel/expert in radiographic image diagnosis in an diagnosis procedure 185. Images can be viewed in many ways, including a single presentation of each simulation, a series of single presentations of simulations for each image, a side-by-side comparison with the original or a standard clinical image, or a side-by-side comparison with other simulations.

Exposure guidelines are generated at an exposure guidelines step 190 based on the viewing and assessment step of diagnosis procedure 185. Guidelines can be made based on, for example, development of a Receiving Operator Characteristic (ROC) curve or a consensus of one or many experts.

The guidelines are translated and applied to technique charts and system tools that help to control dose levels, such as automatic exposure control (AEC), and anatomical programmed radiography (APR).

Automated Assessment of Images

Figure 4:
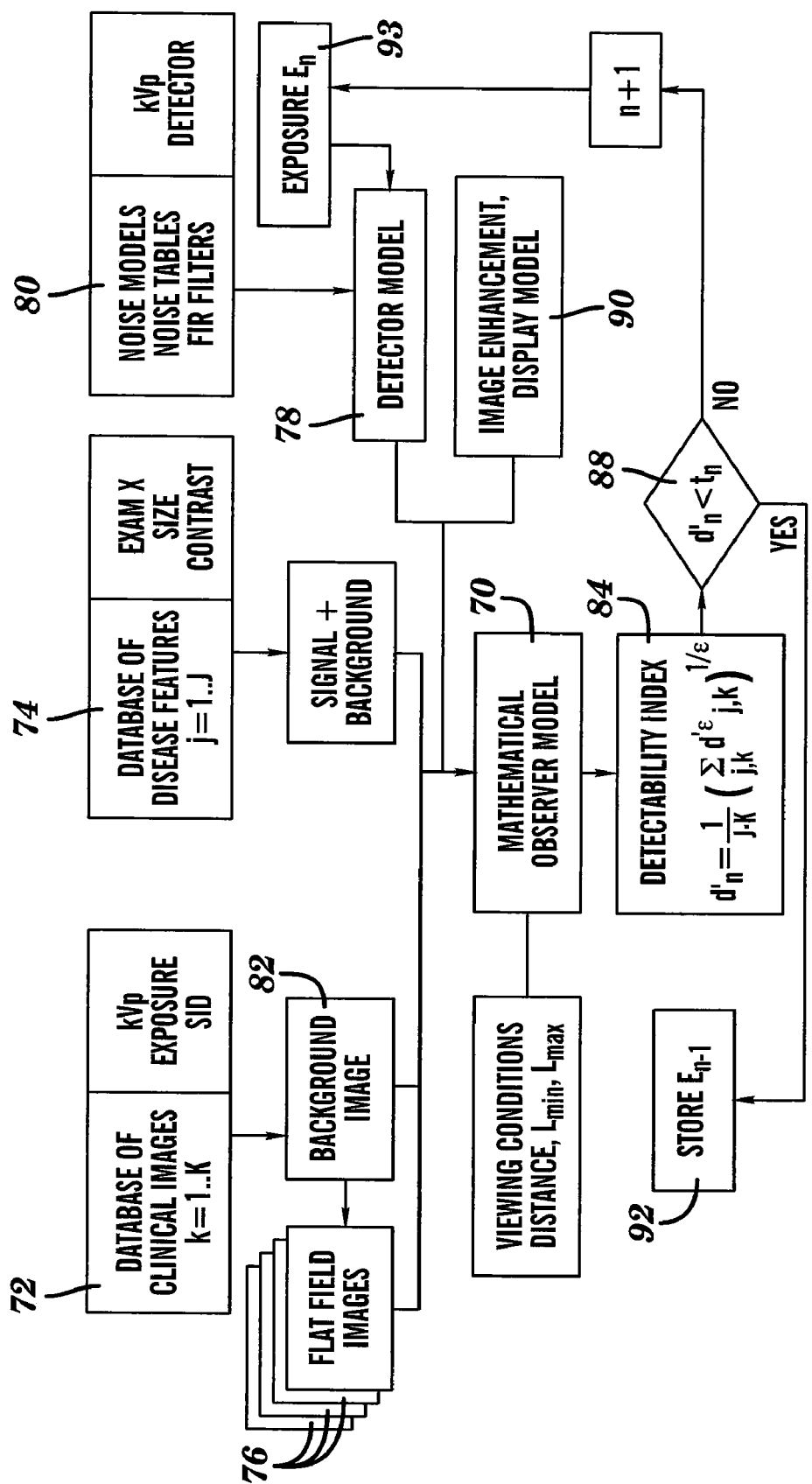
FIG. 4 is a logic flow diagram showing the steps for adding noise to clinical images.

Image assessment can be performed automatically either as a method of validating assessment by a human observer or in order to use an automated computational observer directly for optimizing technique charts, AEC settings, or APR guidelines. Referring to FIG. 4, the operation of a mathematical observer 70 for any single exam type is shown. This same procedure repeats for each exam type x or possible exam types (x=1 . . . X).

Using the procedure shown in FIG. 4, an actual clinical image can be used, providing a more accurate tool for assessment than does a uniform flat-field image. A database 72 of clinical images is used for the optimization. These are categorized and indexed by exam type and technique information such as, for example, the generator voltage (kVp), exposure (mAs) and source-to-image distance (SID) stored with the images. For each exam type x, there are K clinical images (k=1 . . . K) available. Likewise, there is a database 74 of available disease features. The disease features may be varied in size by interpolation and contrast by subtracting the mean or median, scaling, and adding the mean or median value back in. Alternatively the disease features can be generated using a set of equations so that a size and contrast can be specified as input parameters to the equations. A set of flat field images 76 is also provided as input for obtaining some information about noise inherent to the exposure level.

Another database 80 includes noise tables and FIR filters for different kVp settings, which are passed to a detector model 78. The detector model 78 scales the images to the desired exposure $E_n$ 93 and adds noise. In step 90, image processing representative of the exam type is performed and the images are passed through the display model, which adds blur, noise and other image degradations characteristic for the display. If the system to be optimized is different from the system on which the database clinical images were captured, the database must store noise tables and FIR filters for both systems.

Programmed control logic loops over the images by exam type, using the stored disease features that are possible for the exam type (j=1 . . . J) and exposure settings (n=1 . . . N) at or below the exposure that produces noise levels equivalent to those in the stored clinical image. For each iteration, a random portion (for example, 1.7 cm×1.7 cm) in one embodiment, is cropped from the clinical image as a background image 82. Background image 82 has the disease feature placed in the center and M noise fields (flat fields at the median of the background image) are passed through the overall imaging chain representing the system. This set of images is analyzed by the mathematical observer model 70 and a detectability index d' 84 is calculated. The mathematical observer quantifies the visibility of a signal against a background and in the presence of noise, using the detectability index (d') from signal detection theory. The d' metric is well known in medical imaging (M. P. Eckstein, C. K. Abbey, F. O. Bochud, "A Practical Guide to Model Observers for Visual Detection in Synthetic and Natural Noisy Images," In J. Beutel, H. L. Kundel, and R. L. Van Metter (eds.), *Handbook of Medical Imaging: Volume* 1, *Physics and Psychophysics*, Ch. 10, p. 593, SPIE Press, Bellingham, 2001. The detectability index (d') is similar to a perceptual signal-to-noise ratio and is similar in magnitude to a 50% just noticeable difference (JND).

The average d' at exposure level $E_n$ is calculated as $$d'_n = \frac{1}{J \cdot K} \left( \sum_{j,k} d'^{\epsilon}_{j,k} \right)^{\frac{1}{\epsilon}}$$

where $\epsilon$ is an exponent and $\epsilon=2$ is the preferred choice.

A set of values $d'_{j,k,n}$ is stored. Mathematical observer model 70 and the images required for mathematical observer model 70 are described in Proc. SPIE 6515, 651512 (2007) "Advanced system model for the prediction of the clinical task performance of radiographic systems", by Karin Töpfer, Brian W. Keelan, and Francisca Sugiro.

To iterate over exposures, the process begins at a high exposure E and terminates if the average detectability index d' falls below a certain threshold, $t_k$ 88 which may be specified as a fraction of the highest d'. Results of visual assessment can be used to confirm whether or not the desired threshold exposure level has been achieved. The threshold exposure determined in this way can be stored as a stored value 92 in the technique chart or it can be used to program the AEC.

In a Graphical User Interface (GUI) implementation, where the captured image and lower dose images are presented side by side, and the system learns over time what the preferred dose is for each exam type, the threshold could be used for preventing the imaging physicist/technologist/radiologist from selecting a dose that is too low. This would provide an indication when the noise is high enough that diagnostically relevant image content could be missed.

The invention has been described in detail with particular reference to certain preferred embodiments thereof, but it will be understood that variations and modifications can be effected within the scope of the invention as described above, and as noted in the appended claims, by a person of ordinary skill in the art without departing from the scope of the invention. While the method of the present invention was developed to help meet the need for reduced dose in projection radiography, this same method could be applied to other modalities such as tomosynthesis, computed tomography, conebeam computed tomography, ultrasound, and gamma radiation imaging. Assessment of images in the method of the present invention can be performed using hard-copy printed images or using images on soft copy display.

Thus, what is provided is an apparatus and method for simulating image noise to provide guidelines for lowering radiation exposure for x-ray images.

PARTS LIST

20 X-ray source
22 A1 filter
26 Exposure
30 Flat-field image
40 NPS
44 Difference NPS
46 Noise tables and FIR filters
48 Noise mask
50 Patient image
52 Exposure scale factor $s_f$
60 Simulated low-dose exposure
66 Image processing
68 Image display
70. Mathematical observer model
72, 74, 80 Database
76 Flat field images 78 Detector model
82 Background image
84 Detectability index d'
88 Threshold
90 Image enhancement display model
92 Stored value
93 Exposure value
94 Technique chart
100 Obtain flat field images step
110 System characterization step
120 Noise definition step
128 Obtain clinical image step
130 Noise adding step
140 Image assessment step
150 Provide exposure guidelines step
170 Collection of clinical images
175 Low-dose simulation process
180 Image processing
185 Expert diagnosis procedure
190 Exposure guidelines step

The invention claimed is:

1. A method for providing an exposure value for radiographic imaging comprising:
obtaining a set of flat-field images at two or more exposure values;
measuring a noise power spectra using the flat field images;
generating at least one noise table according to the noise power spectra interpolated for a set of predetermined exposure values;
transforming exposure values of a clinical image to form a reduced exposure simulation image;
generating a noise mask according to the at least one noise table and exposure values of the reduced exposure simulation image;
adding the noise mask to the reduced exposure simulation image;
assessing the reduced exposure simulation image; and
generating a preferred dose reduction factor.

2. The method of claim 1 further comprising:
generating at least one frequency attenuation component;
applying the at least one frequency attenuation component to the noise mask; and
applying values from the at least one noise table.

3. The method of claim 2 wherein the frequency attenuation component is a finite impulse response (FIR) filter.

4. The method of claim 1 wherein assessing the reduced exposure simulation image comprises comparing human and computational observer assessments.

5. The method of claim 1 wherein the flat-field images are obtained from an image modality selected from the group of projection radiography, tomosynthesis, computed tomography, conebeam computed tomography, ultrasound, and gamma radiation imaging.

6. The method of claim 1 further comprising employing the dose reduction factor to provide at least one value in a technique chart.

7. The method of claim 1 further comprising employing the dose reduction factor to provide an automatic exposure control setting.

8. The method of claim 1 further comprising employing the dose reduction factor to provide an anatomical programmed radiography setting.

9. The method of claim 1 further comprising applying the preferred dose reduction factor to a subsequent exposure.

10. The method of claim 1 wherein the steps of obtaining the set of flat-field images, measuring the noise power spectra, and generating the at least one noise table are performed at one or more x-ray spectra.

11. The method of claim 10 wherein different beam energy and filtration values are used for obtaining the different flat field images.

12. The method of claim 1 where the beam energy and filtration values of the clinical image differ from the beam energy and filtration values at which the noise tables were made.

13. The method of claim 1 wherein assessing the simulation image is accomplished by a human observer.

14. The method of claim 1 wherein assessing the simulation image is accomplished by a mathematical observer.

15. The method of claim 1 wherein assessing the simulation image further comprises obtaining a hardcopy of an image.

16. The method of claim 1 wherein assessing the simulation image further comprises obtaining a softcopy display of an image.

17. The method of claim 1 wherein the exposure values of a clinical image to form a reduced simulation exposure image are transformed using a 1-dimensional lookup table based on the exposure values of the clinical image.

18. The method of claim 1 wherein the exposure values of a clinical image to form a reduced simulation exposure image are transformed using a 3-dimensional lookup table based on exposure values and horizontal and vertical location in the clinical image.

19. The method of claim 1 wherein image processing is applied to the simulation image to enhance presentation of an image prior to assessing an image.

* * * * *